United States Patent
Arroteia et al.

(10) Patent No.: US 10,966,917 B2
(45) Date of Patent: Apr. 6, 2021

(54) COMPOSITION COMPRISING GUAÇATONGA EXTRACT AND AROEIRA EXTRACT, USE THEREOF AND A METHOD FOR PREVENTING AND/OR TREATING SIGNALS CAUSED BY SKIN AGING

(71) Applicant: Natura Cosméticos S.A., Itapecerica da Serra (BR)

(72) Inventors: Kelen Fabiola Arroteia, Campinas (BR); Cintia Rosa Ferrari, Carapicuíba (BR); Renata Hannel Bueloni, Jundiaí (BR); Juliana Carvalhães Lago, Campinas (BR); Rhaisa Thaís Paulineli Navas, São Paulo (BR); Pâmela Araújo Rodrigues Muchiutti, Santo André (BR); Icaro De Assis Santos, Jundiaí (BR); Carolina Iatesta Domenico, Campinas (BR); Daniela Zimbardi, Santa Barbara d'Oeste (BR); Rosa Maria Teixeira Tagé Biaggio, São José dos Campos (BR); Alan Passero, Taboão de Serra (BR); Soraya Baione De Moura, São Paulo (BR); Ana Paula Pedroso De Oliveira, Pompéia (BR)

(73) Assignee: NATURA COSMÉTICOS S.A., Itapecerica da Serra (BR)

( * ) Notice: Subject to any disclaimer, the term of this patent is extended or adjusted under 35 U.S.C. 154(b) by 192 days.

(21) Appl. No.: 14/917,876

(22) PCT Filed: Sep. 8, 2014

(86) PCT No.: PCT/BR2014/000316
§ 371 (c)(1),
(2) Date: Mar. 9, 2016

(87) PCT Pub. No.: WO2015/031971
PCT Pub. Date: Mar. 12, 2015

(65) Prior Publication Data
US 2016/0220476 A1 Aug. 4, 2016

(30) Foreign Application Priority Data
Sep. 9, 2013 (FR) .................................. 13 58641

(51) Int. Cl.
*A61K 36/00* (2006.01)
*A61K 8/97* (2017.01)
*A61Q 19/08* (2006.01)

(52) U.S. Cl.
CPC ............. *A61K 8/97* (2013.01); *A61Q 19/08* (2013.01)

(58) Field of Classification Search
None
See application file for complete search history.

(56) References Cited

U.S. PATENT DOCUMENTS

2002/0064538 A1   5/2002   Chang et al.
2004/0258676 A1   12/2004  Perrier et al.

FOREIGN PATENT DOCUMENTS

| JP | 2003095969 | 4/2003 |
| KR | 100848800 | 7/2008 |
| WO | WO 2006/053415 A1 | 5/2006 |
| WO | WO 2011/020167 A1 | 2/2011 |
| WO | WO 2015/031971 A2 | 2/2011 |

OTHER PUBLICATIONS

Matsuo et al. (2011) BBRC 411: 449-454.*
da Silva et al. (2008) ACTA Amazonica vol. 38(1): 107-112.*
Albano et al. (2013) Journal of Ethnopharmacology 147; 612-617. (Year: 2013).*
Carvalho et al. (2013) Rev. Bras. Pl. Med., Botucatu, v. 15, n. 1, p. 158-169. (Year: 2013).*
dos Santos et al. (2009) Journal of essential oil-bearing plants, Jan. 2009, 10 pages (Year: 2009).*
El-Massry et al. (2009) J. Agric. Food Chem. 57, 5265-5270. (Year: 2009).*
Lipinski et al. (2013) Antibacteril activity of Caesaria Sylvestris, Schinus Terebinthifolius and Tabebuia Avellandedae—three brazilian tree speces. PUBVET, Londrina, V. 7, N. 21, Ed. 244, Nov. 2013 (Year: 2013).*
Mattos et al. (2007) J. Ethnopharmacology 112: 1-6. (Year: 2007).*
International Search Report for PCT/BR2014/000316 dated Jun. 26, 2015.
Database GNPD [Online] Mintel; Feb. 2009 (Feb. 2009), "Brazilian Pepper Bar Soap", XP002724066, Database accession No. 1046373 abstract.
Database GNPD [Online] Mintel; Nov. 2006 (Nov. 2006), "Foot Cream", XP002724067, Database accession No. 609071 abstract.

(Continued)

*Primary Examiner* — Russell G Fiebig
(74) *Attorney, Agent, or Firm* — Alston & Bird LLP

(57) ABSTRACT

The present invention relates to a cosmetic composition comprising guacatonga extract (*Casearia silvestris*), aroeira extract (*Schinus tere-binthifolius raddi*) and cosmetically acceptable adjuvants, for preventing and/or treating signs of skin aging. It further relates to the use of guagatonga extract (*Casearia silvestris*) and aroeira extract (*Schinus terebinthifolius raddi*) in the preparation of a cosmetic composition for preventing and/or treating signs of skin aging, as well as the use of this composition for simultaneously increasing tropoelastin, increasing the lysyl exidase (LOX) enzyme and reducing the activity of elastase in the dermis. The invention relates to a method of preventing and/or treating signs of skin aging, which comprises applying said cosmetic composition to the skin. Finally, the invention relates to a method of preparing said composition according to the present invention.

4 Claims, 8 Drawing Sheets

(56) References Cited

OTHER PUBLICATIONS

Esteves I et al: "Casearia sylvestris sw. essential oil activity in inflammation in rats induced by bothrops alternatus venom", International Journal of Pharmaceutical Sciences Review and Research, Bangalore: Global Research Online, IN, vol. 7, No. 2, Mar. 2011 (Mar. 2011), pp. 28-32, XP002724068, ISSN: 0976-044x the whole document.
International Preliminary Report on Patentability for PCT/BR2014/000316 dated Mar. 10, 2016.

\* cited by examiner

COMPOSITION COMPRISING GUAÇATONGA EXTRACT AND AROEIRA EXTRACT, USE THEREOF AND A METHOD FOR PREVENTING AND/OR TREATING SIGNALS CAUSED BY SKIN AGING

FIELD OF THE INVENTION

The present invention refers to the use of plant technology relating to the Brazilian biodiversity for increasing the formation of the functional classic system of the skin, comprising a combination of Guaçatonga (*Casearia sylvestris*) extract and Aroeira (*Schinus terebinthifolius raddi*) extract. The present invention refers also to a multiple action mechanism, i.e, deposition of elastin by increasing elastin and lisyl oxidase (LOX), and reduction of its degradation by inhibiting the enzyme elastase. The present invention refers particularly to the use of said technology in cosmetic compositions for the treatment of skin aging signs.

BACKGROUND OF THE INVENTION

The skin covers the surface of the human body and is constituted by an epithelial portion, the epidermis, and a conjunctive portion, the dermis. The skin is one of the largest organs of the human body and performs multiple functions such as protecting the organism against the loss of water and against friction, transmitting information on the environment to the central nervous system, cooperating with the thermoregulation of the body and excreting several substances, among others.

The epidermis is constituted by a keratinized stratified squamous epithelium.

The dermis, in turn, is constituted by a conjunctive tissue, on which the epidermis rests and joints the skin to the subcutaneous tissue. The dermis has a thickness that varies according to the region observed, reaching a maximum of 6 mm.

The dermis is constituted essentially by two layers: the superficial papillary one and the deeper reticular one.

The papillary layer is thin, constituted by a loose conjunctive tissue, forming the dermal papillae. Here are special collagen fibrillae present, which are inserted from one side into the basal membrane and penetrate deeply into the dermis by the other side. These fibrillae aid in fixing the dermis to the epidermis.

The reticular layer, in turn, is thicker, and is constituted by a dense conjunctive tissue. Both layers contain many fibers of the elastic system, responsible for the skin elasticity.

The elastic fibers or elastin fibers are the main components of the elastic system of the skin. These fibers are formed by polymerization (junction or cross-link) of monomers called tropoelastin, the latter being a precursor of elastin. This process of polymerization is not spontaneous and depends on the actuation of the lysyl oxidase enzyme (LOX), which aid in polymerizing tropoelastin to elastin. On the other hand, the elastase enzyme is the enzyme that degrades the elastin fibers of the skin.

During the aging of the skin and with the constant incidence of UV radiation to which it is exposed over the years, there is a reduction in the mechanisms that form elastin, thus reducing the amount of elastin in the skin. Concomitantly, there is an increase in the degradation of these proteins due to the increase in the elastase enzyme, which is responsible for this degradation.

The products intended for retarding and/or improving the symptoms of skin aging, which already exist on the market, do not have a composition that raises the action mechanism proposed by the present invention. Besides, there is no description, in the prior art, of a product comprising specifically the guaçatonga and aroeira extracts for the purpose of retarding and/or improving the symptoms of skin aging according to the present invention. There are a few products that have the objective of increasing the production of elastin in the skin. However, there is no proof that there is effectively an increase in the deposition of elastin—for instance, only an increase in soluble tropoelastin is proven, without proving the actual deposition. Sometimes one talks of the increase in collagen or the reduction of collagenase in the skin, and that this, in some way, would enhance the elasticity of the skin. Such a concept is mistaken, since the collagen fibers are related to the firmness of the skin, not to its elasticity. There are also a few products that promise the increase of the LOX enzyme and, as a result, an increase of the functional elastin in the skin. However, there is no evidence of the increase in the protein tropoelastin and of functional elastin. A few products work only with the anti-elastase mechanism in isolated form, while others do not prove the action mechanism in the elastic system.

There are still products that are used for the purpose of being anti-elastase or, in most cases, the protection of elastin, but in isolated form, without proving an increase in the amount of elastin and of in the deposit thereof. There are still products that contain elastin hydrolysates in their composition and, in this way, they promise an increase in skin elasticity and in the capability thereof to regenerate and produce elastin. This concept is mistaken, because elastin does not penetrate the skin and so the promised effect is not achieved.

Finally, there are still products that promise an improvement in the functionality of the elastic fiber by means of the Dill seed extract, and it is said that this extract increases the concentration of LOX. However, the increase in the concentration of LOX alone does not guarantee an increase in elastin.

Thus, it is possible to note that no product available on the market has a multifocal approach that acts on multiple mechanism of the elastic system for deposition of functional elastin, as the composition comprising the plant extracts of guaçatonga and aroeira proposed by the present invention.

With regard to prior-art documents in the technological field of the present invention, document US 2004/0258676 relates to a composition for regulating elastogenesis in cases of abnormal or pathological elastogenesys, comprising an isoform of the LOX enzyme, as well as a screening methodology for selecting compositions capable of acting on the elastogenesis (formation of elastin). Said document, unlike the present invention, relates to the stimulation of the activity of the LOX enzyme only in cases of pathogenic or abnormal or elastogenesis-defficient states, such as fibrosis or solar elastosis. On the other hand, the present invention relates to a specific combination of guaçatonga and aroeira extracts, which works in conjunction with three biologic mechanisms specifically directed to the elastic system of the skin, namely, increase in tropoelastin (elastin precursor), increase in the LOX enzyme in healthful and normal cells, and reduction of the elastase activity. In spite of describing the actuation on one of the enzymes related to the elastic system of the skin, there is no mention or suggestion in said document, about the combined use of guaçatonga and aroeira, let alone for actuation on the elastic system as a whole. Said document does not describe either the stimulation of the activity of the LOX enzyme in a state other than pathogenic or abnormal.

Document US 2002/064538, in turn, discloses a method for controlling skin elasticity comprising a step of using a compound that inhibits or induces the expression of tropoelastin mRNA or protein in keratinocytes. Said document claims only the modulation of tropoelastin. Said document does not describe the reduction of elastase activity or the increase in deposition of elastin on the skin. Besides, the plant extracts used in the present invention are not used or even suggested as possible components of the composition disclosed in the prior art. Said document does not describe either the combined use of guaçatonga and aroeira in actuation on the elastic system as a whole.

On the other hand, document WO 2006/053415 discloses the supply of plant extracts listed in Tables 1 to 5 and the dermatologic uses thereof with an inhibiting effect on the MMP1, 3, 9 proteases and elastase of human leucocytes. However, said document is directed only to the inhibition of proteases. Contrarily, the present invention, as already mentioned above, has a multifocal approach on the elastic system, with a view to increase the deposit of elastin on the skin and, at the same time, prevent the degradation thereof with the combined use of aroeira and guaçatonga. The document in question does not cite the increase in deposition of elastin on the skin, and the composition of the plant extracts used in that invention are not comprised within the combination of the present invention.

SUMMARY OF THE INVENTION

The present invention relates to a cosmetic composition comprising from 0.0001 to 10%, by weight of the total composition, of a guaçatonga (*Casearia sylvestris*) extract, from 0.00005 to 10%, by weight of the total composition, of an Aroeira (*Schinus terebinthifolius raddi*) extract and cosmetically acceptable adjuvants, intended for the prevention and/or treatment of signs caused by skin aging.

The present invention further comprises the use of Guaçatonga (*Casearia sylvestris*) extract and of Aroeira (*Schinus terebinthifolius raddi*) extract in the preparation of a cosmetic composition for preventing and for treating signs of skin aging, as well as the use of this composition for simultaneous increasing tropoelastin, increasing the lysyl oxidase enzyme (LOX) and reducing the activity of elastase in the dermis.

The present invention further relates to a method of preventing and/or treating signs of skin aging, which comprises the application of said cosmetic composition to the skin.

The present invention further comprises a method of preparing said cosmetic composition according to the present invention.

DETAILED DESCRIPTION OF THE INVENTION

Figure 1:
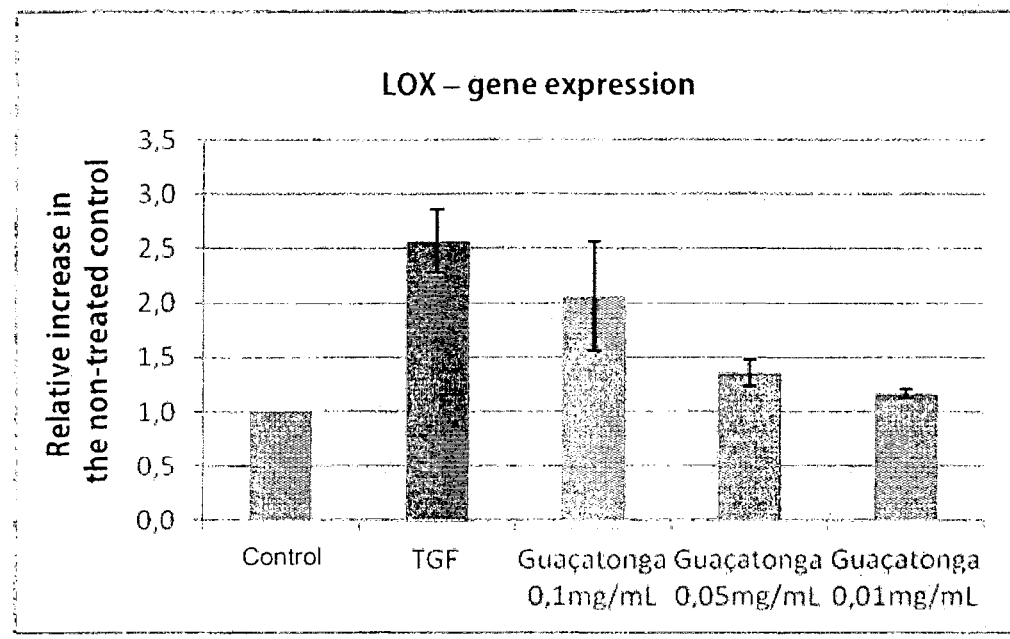
FIG. 1 represents a comparative analysis of the relative LOX gene expression between a control group and a group treated with different concentrations of the sample of guaçatonga extract.

The present invention relates to the use of plant extracts for increasing the formation of elastin and reducing the degradation thereof, thus reversing the condition generated by skin aging. As already mentioned above, during the aging there is a reduction on the formation of elastin on the skin and, at the same time, the increase in degradation of this protein, which causes reduction of the skin elasticity and a tendency to formation of wrinkles and flaccidity. The present invention provides a composition comprising plant extracts that enhance the formation of elastin and reduce the degradation thereof, thus improving the appearance of the skin treated with the technology according to the present invention.

The technology according to the present invention acts on three biologic mechanisms closely related to the elastic system of the skin: increase of tropoelastin (elastin precursor), increase of the LOX enzyme (the enzyme responsible for cross-linking tropoelastin to form elastin) and reduction of the elastase activity (the enzyme that degrades elastin). Thus, one provides a multifocal approach to the elastic system, with a view to increase the deposition of elastin on the skin and, at the same time, and to prevent the degradation thereof.

According to the present invention, two plant extracts with different and complementary action mechanism are used: gaçatonga (*Casearia sylvestris* extract) and aroeira or "pimeiteira rosa" (*Schinus terebinthifolius raddi*) extract.

The first one acts by increasing the expression of the gene that produces the tropoelastin monomers and also of the gene that produces the lysyl oxidase enzyme (LOX). Thus, the guaçatonga extract increases the expression of genes. This increase in the gene expression leads to the increase of the proteins tropoelastin and LOX. LOX formed acts by linking the tropoelastins formed, leading to effective deposition of the elastin fibre on the skin.

The obtainment of the guaçatonga extract is made by means of autoclaving. The obtainment pathway is aqueous, wherein initially the leaves are dried in an oven and grinded in a knife-mill. In a preferred embodiment, the leaves are placed in an autoclave with water in the ratio of 1:10 (1 part of plant to 10 parts of water). The extraction takes place at a temperature of 121° C., for a period of time of 1 hour. The resulting extracted solution is then filtered in a press filter, by using a raw canvas filtering element, for instance, at room temperature. After the filtration, one adds silicon dioxide (20%) and preserving agents. The aqueous extract is then dried by a spray dryer. The result is a brown refined (powdered) extract of guaçatonga leaf.

The second extract, in turn, acts by inhibiting the activity of the elastase enzyme. More specifically, in the presence of elastase, the extract inhibits the functioning of this enzyme, preventing it from linking to its standard substrate (elastin). Thus, the activity of the enzyme is reduced, that it, said extract contributes to the reduction of the degradation of the elastin (a result of the elastase activity).

The process of preparing the aroeira extract suitable for the present invention is described in patent application WO 2011/020167. The obtainment of the aroeira extract takes place under pressure of water vapor from aroeira leaves. There is then an aqueous extraction under vapor pressure in the ratio of 1:7 (1 part of plant to 7 parts of extracting solvent (water) at a temperature of 85° C. to 150° C., under pressure of 1.60 to 2.40 Kgf/cm2). The resulting solution is then filtered in a press filter at a temperature of 85° C. to 95° C. and concentrated to a reduction by 3 volumes. Then, refining/precipitation with ethanol takes place in the ratio of 1:3, followed by cooling (0° C. to 10° C.) and evaporation of the ethanol. Finally, the filtrate is dried by a spray dryer, giving a refined *Schinus terebinthifolius* extract. The extract obtained is in the form of a powder, dry, brown, containing proteins, flavonoids, cumarins, sugars (20%), condensed tannins (20%) and gallic acid (12%).

Thus, the present invention refers to a cosmetic composition for the prevention and/or treatment of signs of skin aging, comprising from 0.0001 to 10%, by weight of the composition, of a guaçatonga extract, from 0.00005 to 10%, by weight of the composition, of an aroeira extract and cosmetically acceptable adjuvants.

Preferably, the composition according to the present invention comprises 0.005 to 5%, more preferably 0.01 to 1%, by weight of the composition, of a guaçatonga extract and from 0.0005 to 5%, more preferably from 0.00125 to 1%, by weight of the composition, of an aroeira extract.

Hereinafter, a few examples—in a non-restrictive, but rather demonstrative manner—of inert adjuvants and inert agents, compatible with the properties of the composition described herein, which additionally may be employed in the present cosmetic composition:

Water: water is the base of various preferred embodiments of the cosmetic composition of the present invention, acting as a carrier for the other components. The compositions of the present invention comprise preferably demineralized or distilled water in an adequate percentage (q.s.p) to reach 100% of the formula, based on the total weight of the present composition. Of course, other cosmetically acceptable carriers may be used in the present invention;

Antioxidant agents: BHT, BHA, tocoferol and/or derivatives thereof, catechins, tannins and/or derivatives thereof, phenolic compounds, among others;

Preserving agents: methylparabenes, propylparabens, isothiazolinonics, phenoxyethanol;

Film forming agents: agar gum, carrageenan, alginates, Arabic gum, gelatin;

Chelating agents: EDTA, citric acid, etidronic acid; Supporting microcrystalline cross-link forming agents: dextrans, methylacrylates, PHB, PHA;

Polymeric agents and/or copolymeric agents: silicone copolymers, siloxane polymers and/or modified silicone, acrylate copolymers;

Denaturating agents: denatonium benzoate;

Consistency agents: plant waxes, mineral hydrocarbons, paraffin, bee wax, white wax, whale spermaceti, cocoa-nut butter, karite butter, sugarcane wax;

Emollients: liquid paraffin, palm oil, cupuaçu butter, lecithin, milk amino acids, wheat protein, plant protein, plant oils, phospholipids, keramides, *passiflora* keramide, sphyngolipids, lanolin, almond oil, dicapryl carbonate, silicone elastomer, cyclometicone;

Wetting agents and/or hydrating agents: glycerin, propylene glycol, hyaluronic acid, urea, PCA;

Conditioning agents: quaternary ammonium salts, silicones, siloxanes;

Other cosmetic actives, for example, plant extracts, polysaccharides, which have the function of treating skin aging; and UV radiation protective agents (sunscreens): octyl methoxycyanamate, benzophenones, etc.

Said composition is prepared by incorporating simultaneously two extracts into the aqueous fraction of the composition.

The composition according to the present invention may be in the form of different pharmaceutical forms, as for example, cream, gel, suspension or toilet soap.

The present invention further relates to a method for preventing and/or treating the signs of skin aging by means of topical application of the composition according to the present invention.

It is a further object of the present invention to use guaçatonga and aroeira extracts in the preparation of a cosmetic composition to prevent and/or treat the signs of skin aging.

In order to evaluate the effect of enhancing the gene expression of tropoelastin and LOX in cells of skin treated with guaçatonga extract at non-cytotoxic concentrations, one has made the genes quantification by the rt-PCR technique (chain reaction of polymerase via reversed transcriptase) in real time. The results are compared with a non-tested control. The cells used are fibroblast of the RFL line.

The guaçatonga extract produced by the above-mentioned process was weighed and directly solubilized in the culture medium Ham-F12+2% Bovine Fetal Serum. The concentrations tested were 0.1; 0.05 and 0.01 mg/mL for the aqueous sample.

The RFL cell line was incubated with TGF-?, known as LOX expression inductor and ellagic acid, known as tropoelastin inductor, which are the genes of interest for the present invention. Simultaneously, other cells in the same conditions cited above were incubated with guaçatonga extract. The incubation period was of 18 hours. Then, the cell material was collected for extraction of RNA from the cells and synthesis of cDNA. For the reactions of PCR in real time, one used Taqman amplification systems, specific for LOX and tropoelastin, besides the GAPD gene, as endogenous control.

Analysis of the expression relating to LOX is represented in FIG. 1. One presents a comparison between the control group and the group treated with different concentrations of the guaçatonga extract sample. The extract at 0.1 mg/mL had a relative increase of 2 CTs in the gene expression of LOX with respect to the control, which means an increase of 200%.

Figure 2:
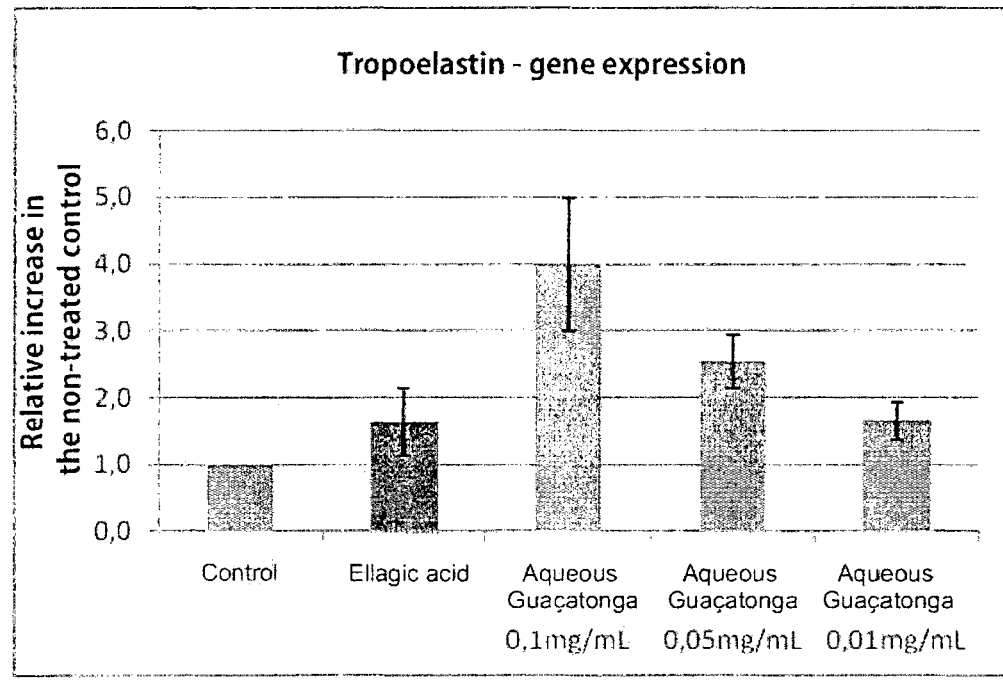
FIG. 2 represents an analysis of the relative tropoelastin gene expression between a control group and a group treated with different concentrations of the sample of guaçatonga extract.

One also carried out an analysis of expression relating to tropoelastin between the control group and the group treated with different concentrations of the guaçatonga extract sample (see FIG. 2). The extract at 0.1 mg/mL had a relative increase of 4 CTs in the gene expression of tropoelastin with respect to the control, which means an increase of 400%.

In order to prove the activity of the aroeira extract present in the composition according to the present invention, the elastase activity (of human neutrophil) was measured by means of a kit, namely "EnzChek Elastase Kit Assay". This Kit has bovine elastin from neck ligament, marked with fluorophore BODIPY FL. The cleavage of this compound by the elastase enzyme generates fluorescent fragments that absorb at 485 nm and emit fluorescence at 535 nm. This makes it possible, by using a spectrophotometer, to monitor the activity of elastase for a period of time. The higher the intensity of fluorescence measured, the greater the cleavage of elastin (therefore, the greater the activity of the elastase enzyme).

The inhibition potential of the elastase of the aroeira extract was compared with the potential of the specific elastase inhibitor, namely N-methoxtysuccinyl-Ala-Ala-Pro-Val-chloromethyl ketone.

The analyses were made with 500 minutes of reaction, that is, 8 hours and 20 minutes, and the elastase was used at the concentration of 0.25 U/ml.

Figure 3:
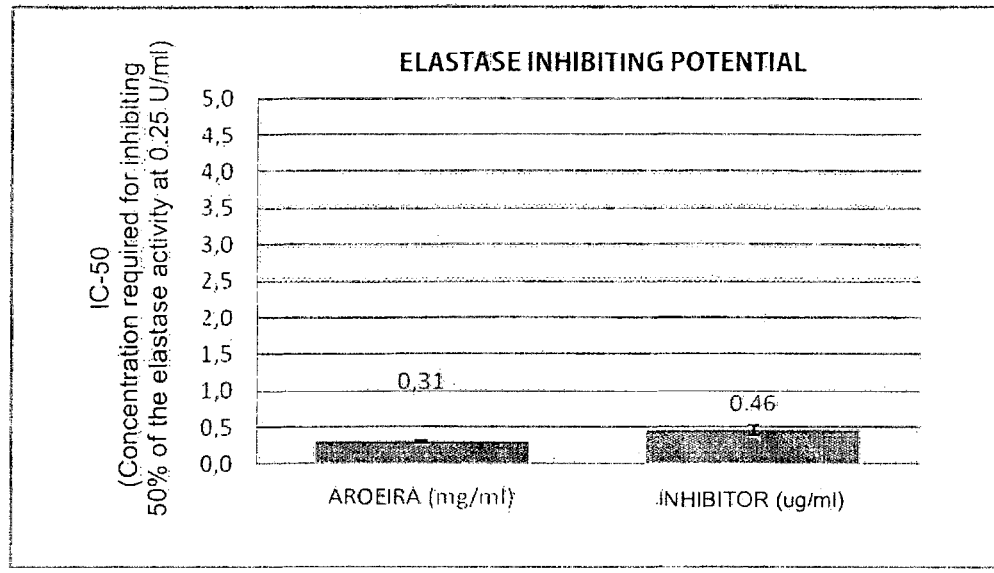
FIG. 3 represents the result of the analysis of activity of elastase through its IC-50 in the presence of the Aroeira extract, as compared with a specific elastase inhibitor.

The aroeira extract exhibited 30% inhibition of the enzyme at a concentration of 0.5 g/mL. Higher concentrations interfere with the assay and could not be tested. The IC50 is 0.31 mg/mL (see FIG. 3).

Figure 4:
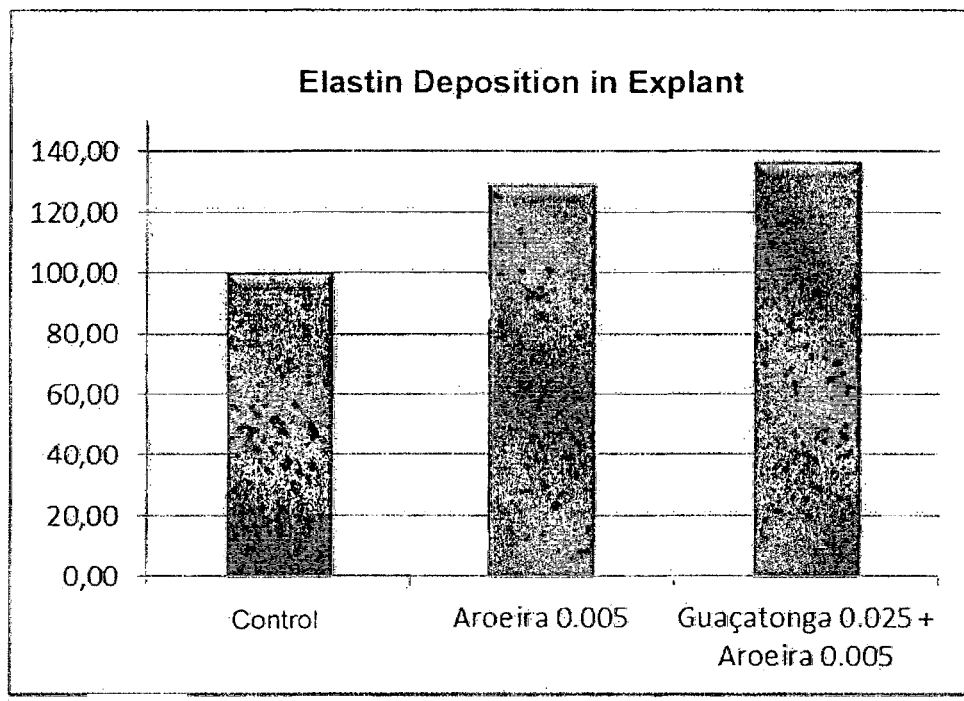
FIG. 4 represents the result of an elastin deposition analysis in human skin explants in the presence of guaçatonga and aroeira extracts, either isolated or in mixtures, in comparison with a non-treated control.
Figure 5:
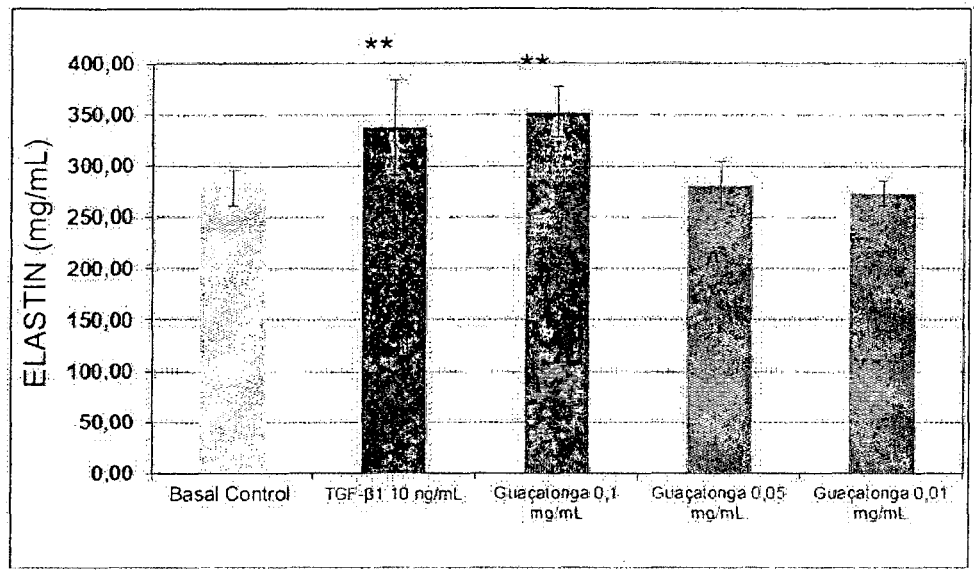
FIG. 5 represents the effect of the guaçatonga extract on the production of tropoelastin (mg/mL) in RFL-6 cells, after 48 hours of incubation. The data represents the average+/− standard deviation (** $p>0.01$ with respect to the control group) (Anova, Dunnet).
Figure 6:
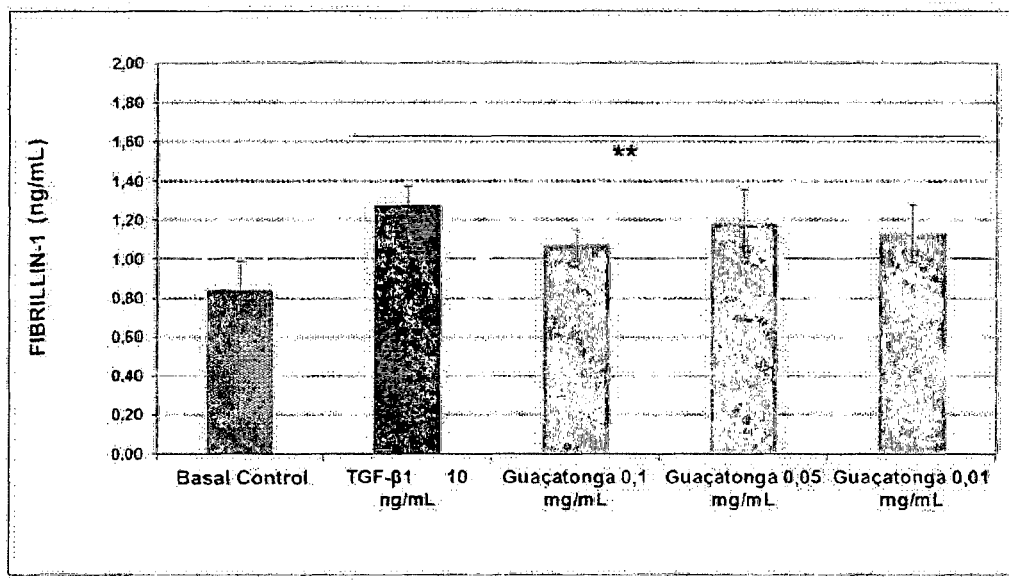
FIG. 6 represents the effect of the guaçatonga extract on the production of Fibriline-1 (ng/mL) in RFL cells. The data represent the average+/−standard deviation (** $p<0.01$ with respect to the control group) (Anova, Dunnet).
Figure 7:
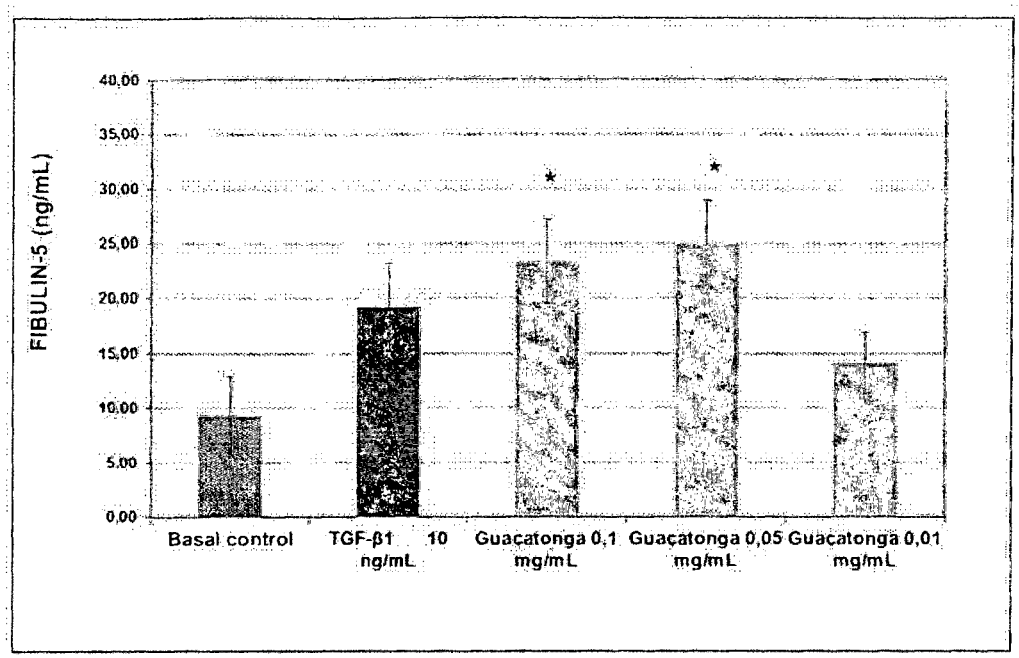
FIG. 7 represents the effect of the guaçatonga extract on the production of Fibulin-5 (ng/mL) in human fibroblasts. The data represent the average+/−standard deviation (** $p<0.01$ with respect to the control group) (Anova, Dunnet).
Figure 8:
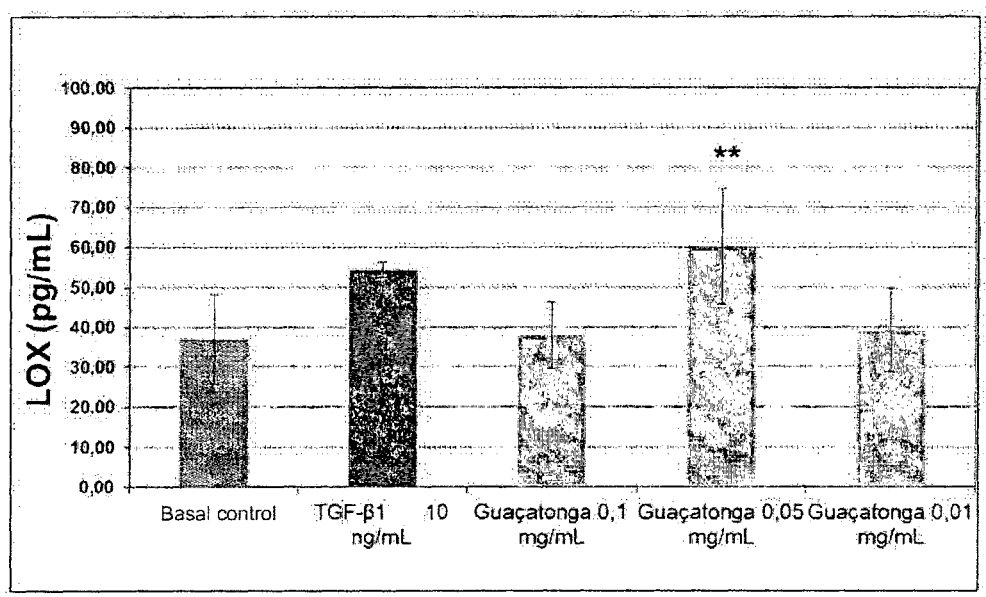
FIG. 8 represents the effect of the guaçatonga extract on the production of LOX (pg/mL) in RFL cells. The data represent the average+/−standard deviation (** $p<0.05$ with respect to the control group) (Anova, Dunnet).

The guaçatonga and aroeira extracts were tested in isolation or in mixtures, for the purpose of demonstrating the increase in the amount or deposition of elastin in human tissue. This test was carried out by treating human skin explants with said extracts. One selected skin fragments from the abdomen of Caucasian women between 20 and 55 years of age, and each condition was tested in biologic triplicate (three different donors). The extracts were diluted in the culture medium and applied to the explants for a 14-day period with 5 changes in this period (24+72+48+48+72+72 hours). Each condition was tested in biologic triplicate (three different donors). After the incubation period, the samples were prepared in standard procedures for histological analysis and colored with Orcein. The quantification of elastin was made by image analysis (24 images per treatment). The guaçatonga and aroeira mixture at concentrations of 0.025 mg/Ml, respectively, provided an increase of 36% in the amount of skin elastin with respect to the control (non-treated explants). The aroeira extract in isolation provided an increase of 29% in elastin (lower than the mixture). The increase in deposited elastin provided by the guaçatonga extract in isolation was not significant, but the mixture of both extracts generated the highest increase in elastin obtained in the test (36%) (see FIG. 4).

Finally, one further carried out assays of protein expression (tropoelastin, LOX, fibulin, fibrillin, and MMP-12) in cell monolayer.

The guaçatonga and aroeira extracts were tested in monolayer cell cultures for the expression of elastin, LOX, Fibrillin-1 (using the RFL lines), MMP-12 and Fibulin-5 (in human skin fibroplasts). The RFL cells are kept in a HAM-F12 medium (Invitrogen, 11765) and the fibroblasts in an RPMI 1640 medium (Gibco, 61870-010), both supplemented with 10% bovine fetal serum. The TFG-β1 factor (10 ng/mL) was used as standard for the protein production test of Elastin, LOX, Fibrillin-1 and Fibulin-5; interleukin-1β (30 ng/mL) and Dexametasone (5 uM), in conjunction, were used as standards for stimulation and reduction of MMP-12. Additionally, ellagic acid (10 ng/mL) was also used in the elastin production test.

The guaçatonga extract was tested at 0.01, 0.05 and 0.1 mg/mL in the tests with fibroblasts (MMP-12 and Fibulin-5), and 0.01, 0.1 and 0.2 mg/mL in the tests with RFL cells (elastin, LOX, Fibrillin-1), respecting the respective cytoxicities in the model (see FIGS. 5 to 9).

The mixtures of guaçatonga (A) and aroeira (B) were tested, respectively, at concentrations of 0.1 mg/mL (A)+0.025 mg/mL (B), 0.05 mg/mL (A)+0.0125 mg/mL (B) and 0.01 mg/mL (A)+0.01 mg/mL (B) in all the tests (elastin, LOX, Fibrillin-1, MMP12 and Fibulin-5) (see FIGS. 10 to 14).

For these tests, the cells kept in wet oven at 37° C. in the presence of 5% CO2, were tripsinized at 80-90% of confluence and seeded on 96-well slides (Nunc, USA). One hour before the treatments, the culture medium was changed to a medium supplemented with 2% bovine fetal serum (basal control) or a medium with 2% bovine fetal serum containing the standards as described above. For the treatments, the samples were weighed and diluted in a culture medium to reach the above-described concentrations, and applied onto the cells for 48 hours. After 48 hours, the supernatant were collected for the respective analysis. The results were analyzed by Anova, followed by Dunnet test, employed when the variance analysis detected significant differences between the groups. In all the studied groups, those whose P values were lower than 0.05 were considered statistically significant.

For the quantification of tropoelastin, one used the Elastin Fastin detection kit (Biocolo, Beslafst, bland), according to the protocol suggested by the manufacturer. The elastin contents of the samples was precipitated in microcentrituge tubes after addition of 1 mL of precipitated reactant (trichloroacetic acid and arginin) and incubated at 0° C. for 24 hours. After the centrifugation of the tubes (10,000×g) for 10 minutes, the supernatant was discarded and the elastin button was re-suspended at 1 mL of TPPS (5, 10, 15, 20-tetraphenyl-21, 23-porfin sulphonate) and 200 uL of saturated ammonium sulfate 90% to form the elastin/dye complex. After 60 minutes of stirring, the tubes were centrifuged again (10,000×g) for 10 minutes, the supernatant was discharged and the complex was re-suspended in 1 mL of the dissociation reactant (HCl guanidine and 1-propanol) thus enabling the formation of the dyed complex, the absorbance of which was measured at 513 nm. The elastin concentration was carried out on the basis of the calibration curve by using the standard of tropoelastin supplied by the manufacturer of the kit.

For quantification of Fibrillin-1, one used the immunoenzymatic assay kit (ELISA sandwich) available commercially (USCN Life Science, E90593Ra). Samples of supernatant of the cell cultures were added to the 96-well slide and incubated at 37° C. for 2 hours. Then, the antibody coupled to biotin was added to the slide, subjected to a new incubation at 37° C. for 1 hour. Then, the slide was washed, avidin conjugated with HRP was added, and the slide was again incubated at 37° C. for 30 minutes. After 20 minutes of reaction, it was interrupted by addition of H2SO4 2N and the reading was carried out on a microslide reader at 450 nm. The fibrillin-1 levels were expressed in ng/mL, calculated from the reference values obtained with a standard curve constructed with known concentrations of the recombinant cytokine.

For quantification of Fibulin-5, one used the immunoenzymatic assay kit (ELISA sandwich) available commercially (USCN LIFE Science, E9315Hu). The assay protocol is the same described for Fibrilin-1. The levels of Fibulin-5 were expressed in ng/mL, calculated from the reference values obtained with a standard curve constructed with known concentrations of the recombinant cytokine.

For quantification of LOX, one used the immunoenzymatic assay (ELISA sandwich) commercially available (USCN Life Science, C92580Ra). The assay protocol is the same described for Fibrillin-1 and Fibulin-5. The LOX levels were expressed in ng/mL, calculated with a standard curve constructed with known values of the recombinant cytokine.

For quantification of MMP-12, the human skin fibroblasts were pre-incubated with IL-1?, for a 6-hour period, and then they were incubated with the active principles and raw materials for 24 more hours, prior to collection of the supernatants. For quantification of MMP-12, one used the immunoenzymatic assay (ELISA sandwich), commercially available (USCN Life Science, E90402Hu). The levels of MMP-12 were expressed in ng/mL, calculated from reference values obtained with a standard curve constructed with known concentrations of the recombinant cytokines.

Figure 9:
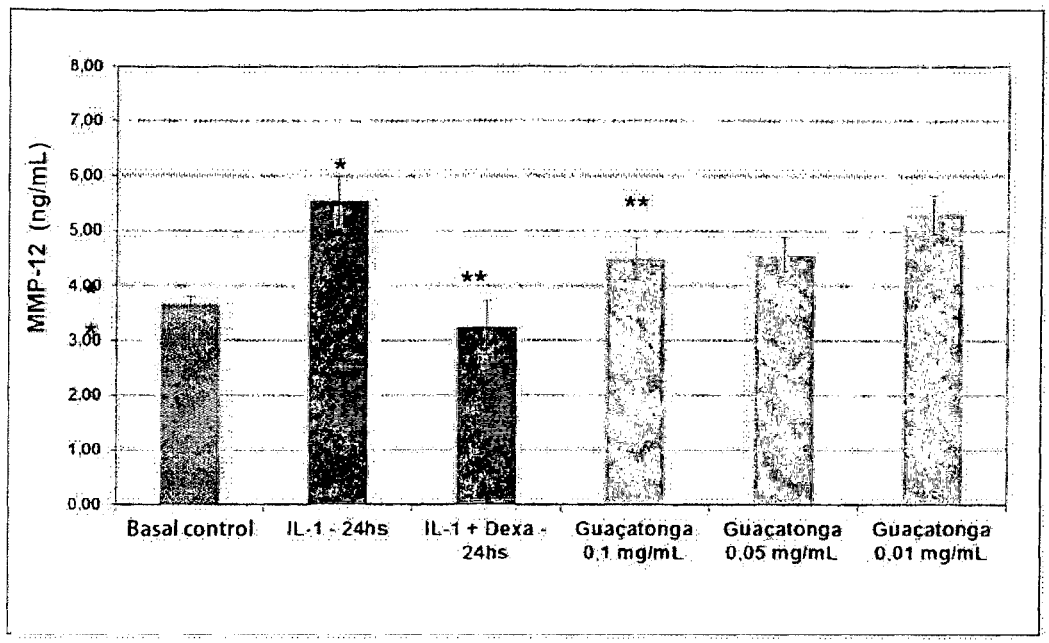
FIG. 9 represents the effect of the guaçatonga extract on the reduction of the production of MMP-12 induced by IL-1b (pg/mL). The data represent the average+/−standard deviation (** $p<0.01$ and * $p<0.05$ with respect to the control group) (Anova, Dunnet).
Figure 10:
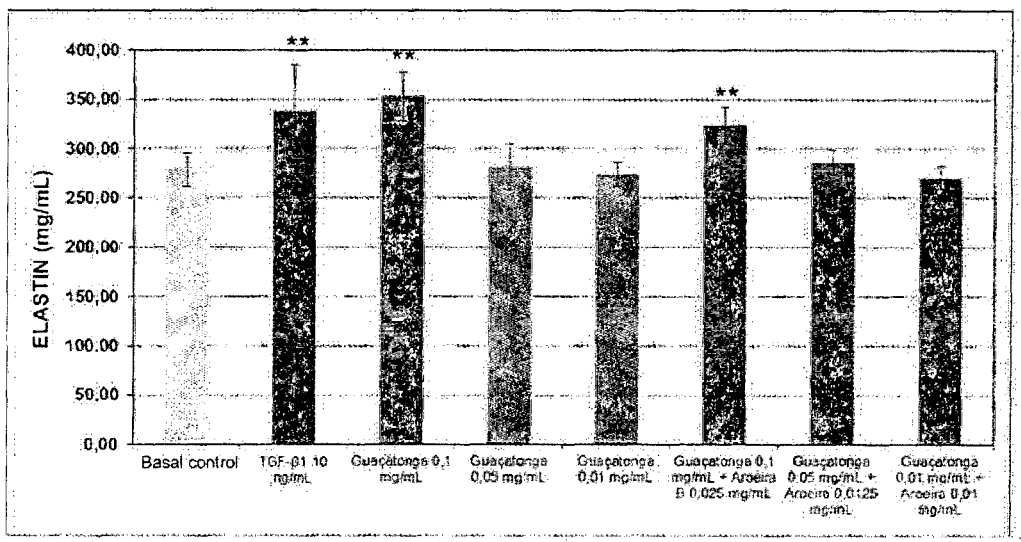
FIG. 10 represents the effect of the guaçatonga extract and of the mixtures of guaçatonga and aroeira on the production of tropoelastin (mg/mL) in RFL-6 cells, after 48 hours of incubation. The data represent the average+/−standard deviation (** $p<0.01$ with respect to the control group) (anova, Dunnet).
Figure 11:
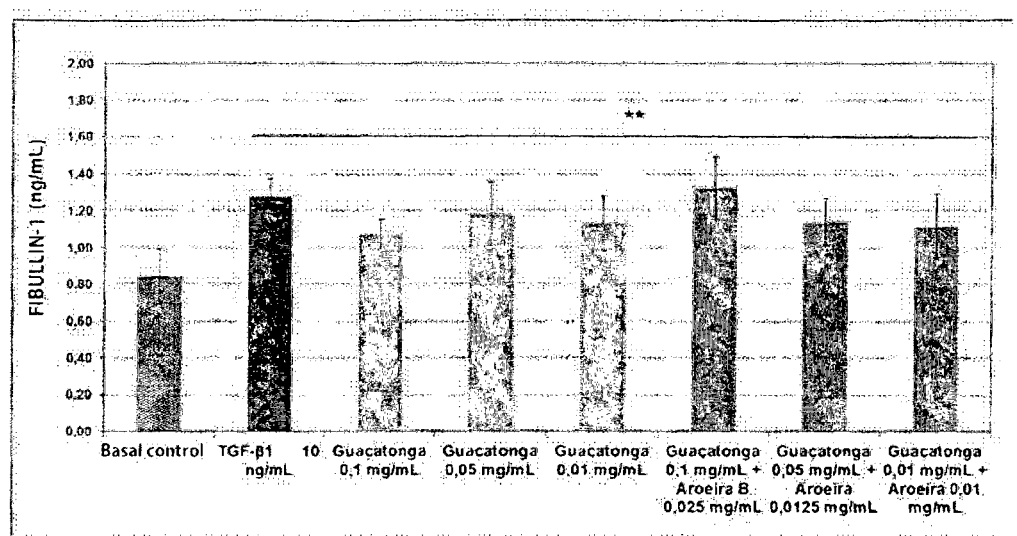
FIG. 11 represents the effect of the guaçatonga extract and of the mixtures of guaçatonga and aroeira (dark green) on the production of Fibriline-1 (ng/mL) in RFL cells. The data represent the average+/−standard deviation (** $p<0.01$ with respect to the control group) (Anova, Dunnet).
Figure 12:
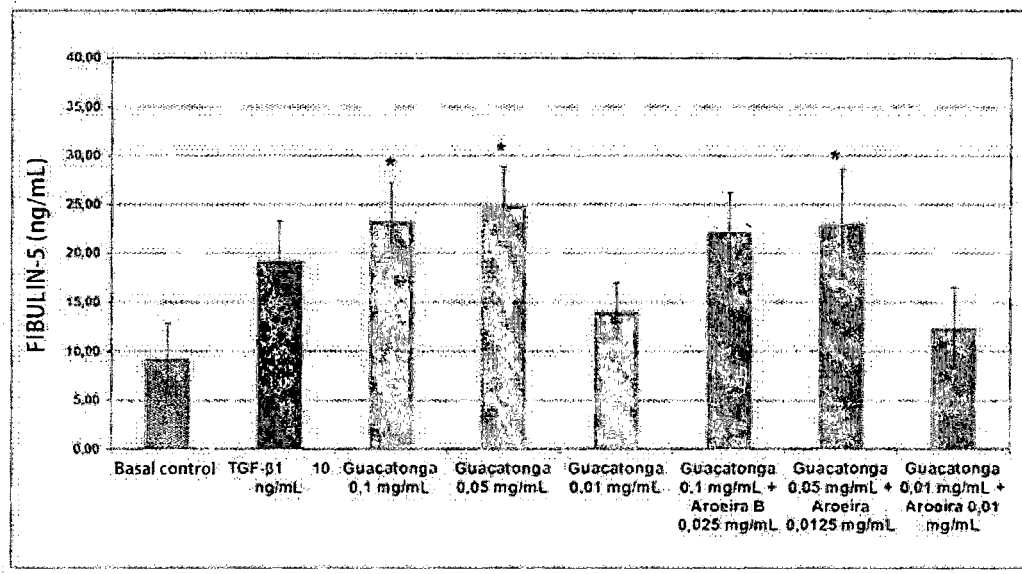
FIG. 12 represents the effect of the guaçatonga extract and of the mixtures of guaçatonga and aroeira on the production of Fibulin-5 (ng/mL) in human fibroblast. The data represent the average+/−standard deviation (** $p<0.05$ with respect to the control group) (anova, Dunnet).
Figure 13:
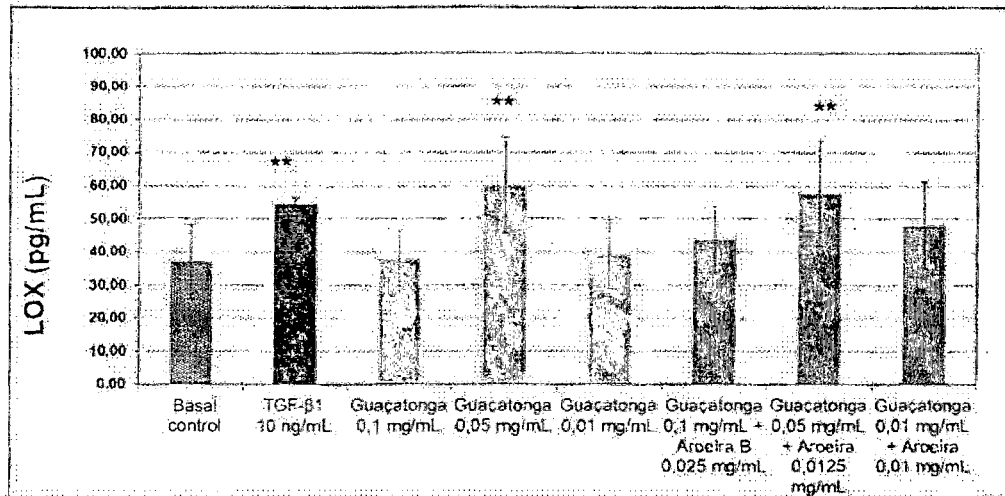
FIG. 13 represents the effect of the guaçatonga extract and of mixtures of guaçatonga an aroeira on the LOX production (pg/mL) in RFL cells. The data represent the average+/− standard deviation (** $p<0.05$ with respect to the control group) (Anova, Dunnet).
Figure 14:
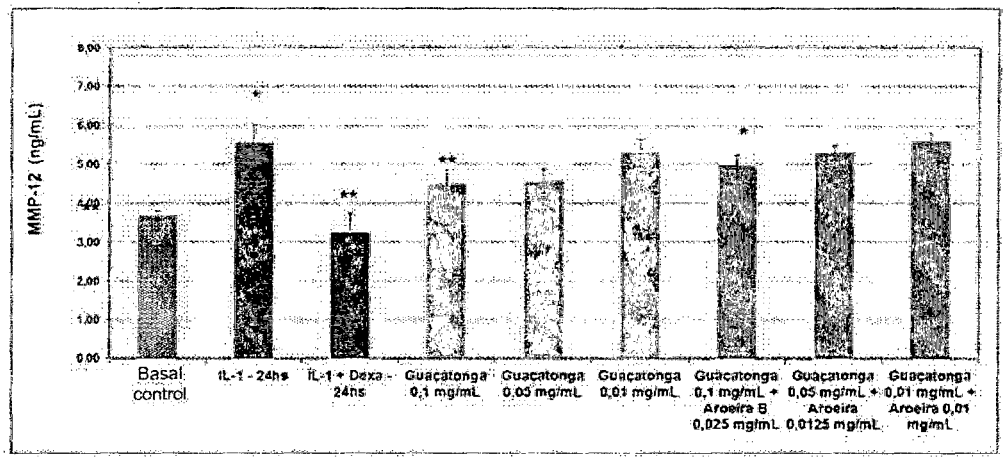
FIG. 14 represents the effect of the guaçatonga extract and mixtures of guaçatonga and aroeira on the reduction of the production of MMP-12 induced by IL-1B (pg/mL). The data represent the average+/−standard deviation (** $p<0.01$ and * $p<0.05$ with respect to the control group) (anova, Dunnet).

The results of the above-mentioned in vitro tests demonstrate that the guaçatonga extract exhibits efficacy in all the final times evaluated and related to the mechanism of deposition of the elastic fiber to the skin, that is, the extract induces the increase in the production of the tropoelastin, Fibulin-5, Fibrillin-1 proteins and of the LOX enzyme (see FIGS. 5 to 8) Further, the extract also acts on the reduction of the protein production of MMP12 (elastase), induced by injury of IL-1, a mechanism that prevents degradation of the elastic fiber (not confirming the gene expression data that suggested an increase in the production of elastase) (see FIG. 9).

The aroeira extract, in spite of inducing the gene expression of tropoelastin and LOX, does not induce the production of the respective proteins. However, the extract exhibits efficacy in the other mechanisms evaluated, which lead to the production of the elastic fiber, like the production of the Fibrillin-1 and Fibulin-5 proteins. Besides, this extract exhibits the difference of inhibiting the activity of the elastase enzyme (biochemical assay) at up to 89% (1 mg/mL). Additionally, for this extract it was possible to observe an increase in the amount of elastic fibers in skin explants, possibly reflecting the potential of protection against degradation of the elastin.

Figure 15:
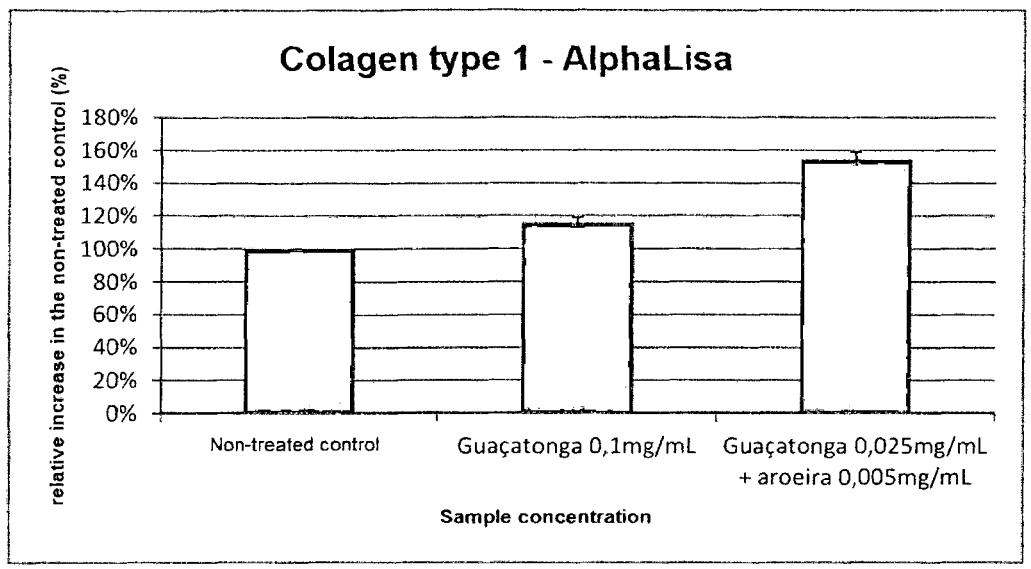
FIG. 15 represents the effect of the guaçatonga extract and mixtures of guaçatonga and aroeira on the synthesis of collagen type 1 in monolayer primary human fibroblastic cells.
Figure 16:
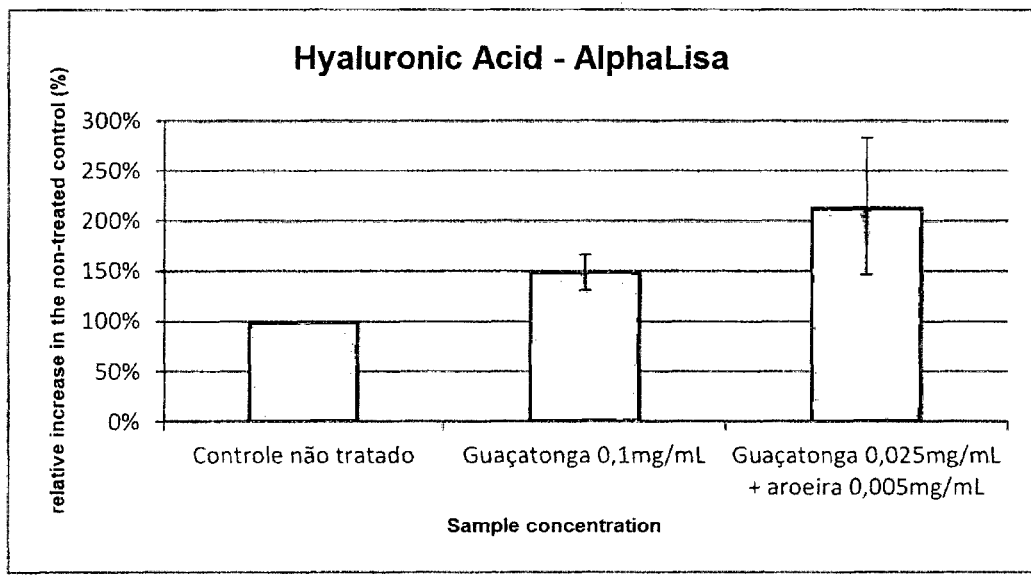
FIG. 16 represents the effect of the guaçatonga extract and mixtures of guaçatonga and aroeira on the synthesis of hyaluronic acid in monolayer primary human fibroblastic cells.

The guaçatonga and aroeira extracts were tested in monolayer cell cultures for the expression collagen type 1 and hyaluronic acid. The mixtures of guaçatonga (A) and aroeira (B) were tested, respectively, at concentrations of 0,025 mg/mL (A)+0.005 mg/mL (B) in comparison with guaçatonga extract at a concentration of 0.1 mg/ml (see FIGS. 15 and 16).

As can be seen, the mixture of guaçatonga and aroeira induced the increase in the synthesis of both collagen type 1 and hyaluronic acid in the cells. These results demonstrate that the combination according to the present invention have a potential in meliorating the skin by stimulating the collagen type 1 and hyaluronic acid synthesis.

In summary, the results demonstrate that the guaçatonga extract is the only sample, among those tested, that exhibits action potential in all the mechanism evaluated (increase in elastin, fibulin-5, fibrillin-1, LOX and reduction of MMP-12). Interestingly, the aroeira extract exhibits the difference of reducing the activity of the elastase enzyme, besides reducing the production thereof, suggesting that the joint use of the samples could modulate the deposition and the degradation of the elastic fibers.

Examples of Formulation According to the Present Invention

Example 1

Emulsion

% by weight of the final composition
Demineralized water—qsp 100
BHT—0.1-1%
Dissodic EDTA—0.05-0.15%
Sodium Benzoate—0.1-0.5%
Aroeira Extract—0.0001-10%
Sodium Acrylic Acid Homopolymer—0.02-0.04%
Xanthan Gum C1911 B—0.3-3.5%
Guaçatonga Extract—0.0001-10%
Tocoferyl Acetate (Vitamin E)—0.5-3%

Example 2

Emulsion

Guaçatonga Extract—0.0001-10%
Propylene Glycol—10-40%
Xanthan Gum C1911 B—0.3-3.5%
Sodium Hydroxide—0.01-0.3%
Sodium Benzoate—0.1-0.5%
Aroeira Extract—0.0001-10%

Sodium Acrylic Acid Homoplymer—0.02-0.04%
Glutathione—0.03-0.04%
Etidronic Acid—0.02-0.04%

The invention claimed is:

1. A cosmetic composition, comprising:
   (a) 0.01 to 1% by weight of the total composition, of guacatonga extract (*Casearia sylvestris*) comprising silicon dioxide;
   (b) 0.00125 to 1% by weight of the total composition, of aroeira extract (*Schinus terebinthifolius raddi*); and
   (c) a cosmetically-acceptable adjuvant selected from the group consisting of: water, antioxidant agents, preserving agents, film forming agents, chelating agents, supporting microcrystalline cross-link forming agents, polymeric and/or copolymeric agents, denaturing agents, consistency agents, emollients, conditioning agents, and UV radiation protective agents.

2. A cosmetic composition according to claim 1, wherein said composition is in the form of a cream, a gel, a suspension or toilet soap.

3. A cosmetic composition according to claim 1, wherein said composition is configured for preventing and/or treating signs of skin aging.

4. A method of preventing and/or treating signs of skin aging comprising applying to skin in need thereof an effective amount of the cosmetic composition of claim 1.

* * * * *